United States Patent [19]

Fehr et al.

[11] Patent Number: 6,025,509
[45] Date of Patent: Feb. 15, 2000

[54] ELEVATED PALMITIC ACID PRODUCTION IN SOYBEANS

[75] Inventors: Walter R. Fehr; Earl G. Hammond, both of Ames, Iowa

[73] Assignee: Iowa State University Research Foundation, Inc., Ames, Iowa

[21] Appl. No.: 09/045,640

[22] Filed: Mar. 23, 1998

Related U.S. Application Data

[62] Division of application No. 08/689,106, Jul. 30, 1996, Pat. No. 5,750,846.

[51] Int. Cl.$^7$ .................................................. C07C 53/00
[52] U.S. Cl. ............................. 554/1; 554/223; 554/224
[58] Field of Search ..................................... 800/200, 255, 800/DIG. 26; 435/415, 426, 430; 47/58, DIG. 1; 554/1, 223, 224

[56] References Cited

U.S. PATENT DOCUMENTS

| | | | |
|---|---|---|---|
| 5,557,037 | 9/1996 | Fehr et al. | 800/200 |
| 5,602,311 | 2/1997 | Fehr et al. | 800/200 |

OTHER PUBLICATIONS

"Inheritance of Altered Palmitic Acid Percentage in Two Soybean Mutants", *Journal of Heredity*, E.A. Erickson et al., vol. 79, pp. 465 to 468 (1988).

"Inheritance of Reduced Palmitic Acid Content in Seed Oil of Soybean", *Crop Science*, W. R. Fehr et al., vol. 31, No. 1, pp. 88 to 89 (1991).

"Inheritance of Elevated Palmitic Acid Content in Soybean Seed Oil", *Crop Science*, W. R. Fehr et al., vol. 31, No. 6, pp. 1522 to 1524 (1991).

"Inheritance of Reduced and Elevated Palmitate in Mutant Lines of Soybean", *Crop Science*, Steven R. Schnebly et al., vol. 34, pp. 829 to 833 (1994).

"Inheritance of Palmitic and Stearic Acid Mutants of Soybean", *Crop Science*, D. M. Bubeck et al., vol. 29, pp. 652 to 656 (1989).

"Registration of C1726 and C1727 Soybean Germplasm With Altered Levles of Palmitic Acid", PI532834—Reg. No. GP–117, *Crop Science*, vol. 30, p. 240 (Jan.–Feb. 1990).

"Registration of 'Kenwood' Soybean", PI537094—Reg. No. 253, *Crop Science*, vol. 30, p. 1162 (Sep.–Oct. 1990).

*Primary Examiner*—Deborah Carr
*Attorney, Agent, or Firm*—Burns, Doane, Swecker & Mathis, L.L.P.

[57] ABSTRACT

Soybeans (ie., *Glycine max* L. Merr.) possessing a novel genetic determinant for the enhanced production of palmitic acid in the endogenously formed vegetable oil of the seeds are provided. Such genetic determinant is the homogeneous recessive fap5fap5 gene pair that has been found to be capable of formation through mutagenesis. Once formed, such genetic determinant can be readily transferred to other soybean lines and cultivars where it is similarly expressed on a reliable basis under conventional field growing conditions. In a preferred embodiment when a soybean plant possesses the combined presence of the homogeneous recessive genes (1) fap2-bfap2-b, (2) fap4fap4, as well as (3) fap5fap5 for enhanced palmitic acid formation in the seeds, it has been found that an unusually high expression for palmitic acid production in the resulting vegetable oil of the seeds is provided that is in excess of 30 up to approximately 37 percent by weight based upon the total fatty acid content. A resulting vegetable oil is made possible in this instance that is particularly well suited for margarine preparation in absence of the need for hydrogenation.

6 Claims, No Drawings

ELEVATED PALMITIC ACID PRODUCTION IN SOYBEANS

This application is a divisional, of application Ser. No. 08/689,106, filed Jul. 30, 1996, now U.S. Pat. No. 5,750, 846.

This invention was made with government support under grant numbers 91-34258-5998 and 94-34258-0080 awarded by the United States Department of Agriculture. The government has certain rights in the invention.

BACKGROUND OF THE INVENTION

Soybean (ie., *Glycine max* L. Merr.) seeds are recognized to represent one of the most important oilseed crops presently being grown in world. Such seeds provide an excellent source of vegetable oil as well as a source of protein that can serve as an alternative to animal meat products. For instance, tofu and soymilk derived from soybean seeds provide a major source of protein for the people of China and Southeast Asia.

Soybean oil obtained from soybean seeds commonly is utilized in the production of plastic fats suitable for human consumption (e.g., as margarines and shortenings). Such plastic fats frequently comprise a matrix of solid fats wherein interstices present therein are filled with liquid oil. It is recognized that solid fats can crystallize in several forms having different melting points and differing physical properties. These forms commonly are designated $\alpha$, $\beta'$, and $\beta$, with the $\beta'$ crystalline form having the highest melting point and highest stability. Other forms additionally can be present. The $\beta'$ crystalline form generally has properties that most commonly are sought in a plastic fat. When the solid portion of the plastic fat contains approximately 15 percent by weight or more of palmitic acid (C16:0) and the remainder is stearic acid (C18:0), it commonly will assume the most advantageous $\beta'$ crystalline form. However, if the ratio of stearic acid to palmitic acid is higher, then the fat may more readily convert to the less advantageous $\beta$ form having less desirable physical characteristics.

It generally is recognized that endogenously formed soybean oil commonly will contain a palmitic acid concentration on the order of 12 percent or less by weight based upon the total fatty acid content following the simple crushing and extraction of soybean seeds and the use of a standard analysis technique. It will be recognized by those skilled in the relevant area of technology that the fatty acids commonly are primarily present while esterified with glycerol in the vegetable oil. For instance, palmitic acid is provided as palmitate and stearic acid as a stearate. Following the subsequent hydrogenation of unsaturated fatty acids inherently present therein such oil commonly will still crystallize to form the less desirable $\beta$ crystalline form. To prevent this in accordance with prior technology, another oil that is richer in palmitic acid, such as cottonseed oil or palm oil, sometimes is blended with the soybean oil. However, such blending nevertheless has posed difficulties. For instance, some consumers consider palm oil to be undesirable from a health standpoint. Also, cottonseed oil tends to be available in considerably more limited quantities than soybean oil and tends to demand a considerably higher cost than the soybean oil component.

It accordingly has been recognized to be desirable to provide improved plants that endogenously form soybean seeds that include a greater concentration of palmitic acid within the oil present therein on a reliable and readily reproducible basis under conventional field growing conditions while under genetic control.

Palmitic acid levels in soybean seed oil in the past frequently have ranged from 9.3 to 17.4 percent by weight based upon the total fatty acid content as reported by E. A. Erickson et al. in "Inheritance of Altered Palmitic Acid Percentage in Two Soybean Mutants" appearing in the *Journal of Heredity*, Vol. 79, Pages 465 to 468 (1988). Certain mutant soybeans designated C1726 and C1727 were developed through the chemical mutagenesis of the 'Century' variety. It was found that C1726 possessed the fap1fap1 allele or gene pair that expressed a lesser concentration of palmitic acid in the oil that averaged 8.6 percent by weight based on the total fatty acid content. Also, C1727 possessed the fap2fap2 allele or gene pair which expressed a greater concentration of palmitic acid in the oil that averaged 17.3 percent by weight based on the total fatty acid content. The palmitic acid content in the oil of the 'Century' parent prior to mutagenesis was reported to be 11.5 percent by weight based on the total fatty acid content.

A soybean mutant initially designated A1937NMU-173 possessing the fapxfapx allele or gene pair was described by W. R. Fehr et al. in "Inheritance of Reduced Palmitic Acid Content in Seed Oil of Soybean" appearing in *Crop Sci.*, Vol. 31, Pages 88 to 89 (1991). The A1937NMU-173 line subsequently was redesignated as A22 and the fapxfapx gene pair was redesignated as fap3fap3. A mean palmitic acid content in the oil thereof averaged 6.5 percent by weight based on the total fatty acid content.

Mutant soybeans designated A1937NMU-85 possessing the fap2-bfap2-b allele or gene pair and ElginEMS-421 possessing the fap?fap? allele or gene pair were described by W. R. Fehr et al. in "Inheritance of Elevated Palmitic Acid Content in Soybean Seed Oil" appearing in *Crop Sci.*, Vol. 31, Pages 1522 to 1524 (1991). The A1937NMU-85 line, subsequently designated A21, exhibited an elevated pahnitic acid content of 19.8 percent by weight based on the total fatty acid content. The ElginEMS-421 line subsequently was designated A24 and exhibited an elevated palmitic acid content of 17.9 percent by weight based on the total fatty acid content, and the fap?fap? allele or gene pair present therein subsequently was redesignated fap4fap4. Research there reported indicates that the fap2fap2 allele or gene pair and the fap2-bfap2-b allele or gene pair are present at the same locus or are tightly linked. When the fap2-bfap2-b allele or gene pair and the fap4fap4 allele or gene pair are combined in a single plant, a palmitic acid concentration of greater than 25 percent by weight based on the total fatty acid content was reported in the resulting vegetable oil. This line possessing in combination the fap2-bfap2-b allele or gene pair and the fap4fap4 allele or gene pair initially was designated AX4663-5-4-5 and subsequently was redesignated as A19 and is described in commonly assigned U.S. patent application Ser. Nos. 08/375,340, filed Jan. 19, 1995 (now U.S. Pat. No. 5,557,037), entitled "Soybeans Having Elevated Contents of Saturated Fatty Acids," and 08/376, 466, filed Jan. 20, 1995 (now U.S. Pat. No. 5,602,311), entitled "Soybeans and Soybean Products Having High Palmitic Acid Content."

A further discussion of a modified production of palmitic acid in soybean seeds while under genetic control is described by Schnebly et al. in "Inheritance of Reduced and Elevated Palmitate in Mutant Lines of Soybean" appearing in *Crop Sci.*, Vol. 34, Pages 829 to 833 (1994). See also, "Inheritance of Palmitic and Stearic Acid Mutants of Soybean", by D. M. Bubeck et al. appearing in *Crop Sci.*, Vol. 29, Pages 652 to 656 (1989).

It is an object of the present invention to provide under conventional field growing conditions soybean seeds possessing while under genetic control an enhanced level of palmitic acid in the endogenously produced vegetable oil wherein said genetic control is attributable to a new allele.

It is an object of the present invention to provide soybean plants capable upon self-pollination of forming seeds that possess while under genetic control an enhanced level of palmitic acid in the endogenously produced vegetable oil wherein said genetic control is attributable to a new allele.

It is an object of the present invention to provide a vegetable oil derived from soybeans following crushing and extraction that exhibits while under genetic control (as described) an elevated concentration of palmitic acid wherein the level of palmitic acid exceeds that previously available in an endogenously formed soybean seed oil.

It is another object of the present invention to provide in soybeans a novel heretofore unknown homogeneous recessive fap5fap5 gene pair that is capable of elevating palmitic acid production in the endogenously produced vegetable oil present in the seeds thereof.

It is another object of the present invention to combine the homogeneous recessive gene pairs (1) fap2fap2 or fap2-bfap2-b, (2) fap4fap4, and (3) fap5fap5 in a single soybean plant which in combination have been found to make possible the expression while under genetic control of a greater concentration of pahnitic acid in the endogenously formed vegetable oil formed in the soybean seeds of such plant than has heretofore been reported.

It is a further object of the present invention to provide a vegetable oil derived from soybean seeds that contains an elevated endogenously produced saturated fatty acid content while under genetic control which is particularly suited for margarine or shortening production in the absence of hydrogenation.

These and other objects, as well as the scope, nature, and utilization of the claimed invention will be apparent to those skilled in the art from the following detailed description and appended claims.

SUMMARY OF THE INVENTION

Soybean seeds and soybean plants are provided possessing the homogeneous recessive gene pair fap5faps for the expression of an elevated palmitic acid content in the endogenously formed vegetable oil of the seeds. Such fap5fap5 gene pair is present in A27 having ATCC Accession No. 209,222 and can be readily transferred to other soybean plants.

Soybean seeds and soybean plants are provided that exhibit an elevated palmitic acid content in the endogenously formed vegetable oil of the seeds wherein the palmitic acid content is attributable to the combined presence of the homogeneous recessive gene pairs (1) fap2fap2 or fap2-bfap2-b, (2) fap4fap4, and (3) fap5fap5, or a soybean seed descended therefrom that possesses the homogeneous recessive gene pairs. The recessive gene pairs fap2-bfap2-b, fap4fap4, and fap5fap5 in combination are preferred and are present in A28 having ATCC Accession No. 97,672.

A vegetable oil also is provided possessing an elevated palmitic acid content following removal from a soybean seed wherein the palmitic acid concentration is attributable to the combined presence of the homogeneous recessive gene pairs (1) fap2fap2 or fap2-bfap2-b, (2) fap4fap4, and (3) fap5fap5. In a preferred embodiment, the palmitic acid content of the vegetable oil is attributable to combined presence of the gene pairs (1) fap2-bfab2-b, (2) fap4fap4, and (3) fap5fap5.

DESCRIPTION OF PREFERRED EMBODIMENTS

Available soybean varieties typically grown commercially for vegetable oil production in the United States commonly form oils within the resulting soybean seeds under conventional field growing conditions that contain on the order of 10 to 12 percent or less palmitic acid by weight based upon the total fatty acid content. A need has remained for additional soybean plant material that is capable of yielding enhanced levels of palmitic acid in the vegetable oil of the seeds while under genetic control.

It now has been found through empirical research that it is possible to form through mutagenesis soybean plants possessing the novel homogeneous recessive gene pair fap5fap5 for the expression of an elevated palmitic acid content in the endogenously formed vegetable oil of the seeds.

During the formation of the subject fap5fap5 gene pair, a conventional soybean line or cultivar preferably having superior agronomic characteristics for growing at a preselected locale is subjected to such mutagenesis, and selection for the fap5fap5 gene pair is carried out in subsequent generations while observing the plant phenotype for elevated palmitic acid content and conducting inheritance studies in order to ascertain and confirm the different locus for the responsible fap5fap5 gene pair. The ability to form the requisite fap5fap5 gene pair via mutagenesis is not believed to require the selection of a specific soybean starting material. As reported hereafter, good results have been obtained through the mutagenesis of the commercially available 'Kenwood' variety.

Plant cells capable of regeneration (e.g., seeds, microspores, ovules, pollen, vegetative parts) of *Glycine max* L. Merr. are subjected to a mutagenesis treatment during at least one generation, a soybean plant is regenerated from the cells to form soybean seeds in at least one subsequent generation, and selections initially are made on the basis of elevated palmitic acid in the endogenously formed vegetable oil of such seeds. The mutagenesis preferably is carried out under conditions wherein the plant cells are in the form of a soybean seed. Good results have been obtained through the use of a chemical mutagen that heretofore has been recognized to be capable of creating substantial genetic variation in plant material. In a preferred embodiment, ethyl methanesulfonate (EMS) is utilized as the chemical mutagen. Other representative chemical mutagens include N-nitroso-N-methylurea (NMU), sodium azide, 1-methyl-3-nitro-1-nitrosoquanidine (nitrosoquanidine), etc.

In a preferred embodiment wherein seeds are treated, the mutagen concentration and exposure time are selected so as to produce a survival rate in the resulting seeds of approximately fifty percent. Typically approximately 1 ml. of the mutagen solution is provided per seed and the seeds are soaked for several hours while aerating the solution. The seeds next are removed, rinsed with water, and are planted while wet in the field where they are immediately watered.

It has been found that the presence of the fap5fap5 gene pair in an otherwise conventional soybean variety commonly has the ability to alter the phenotype so that the palmitic acid content of the endogenously formed vegetable oil is raised approximately 4 percent by weight based upon the total fatty acid content as determined by gas liquid chromatography. Such elevated palmitic acid content is made available while under such genetic control through the expression of the fap5fap5 gene pair on a reliable basis when the soybean seed-forming plant is grown under conventional field growing conditions for the culture of soybean plants.

Such fap5fap5 gene pair must be provided in the homogeneous recessive form in order to express such elevated palmitic acid content. It further has been demonstrated through inheritance studies that such fap5fap5 gene pair is present at a different locus than previously reported genes for the elevation of palmitic acid content, such as fap2fap2, fap2-bfap2-b, and fap4fap4. For instance, when a plant possessing the fap5fap5 gene pair is crossed with plants possessing such other gene pairs for elevated palmitic acid content, none of the $F_1$ progeny will exhibit the desired level of elevated palmitic acid content in the endogenously produced vegetable oil of the resulting plants and segregation for such desired elevated palmitic acid trait will be manifest in subsequent generations following self-pollination of the resulting $F_1$ progeny as the components of the requisite fap5fap5 gene pair are provided an opportunity to recombine. Also, the presence of such fap5fap5 gene pair in a given soybean plant can be confirmed by crossing such plant with A27 (described hereafter) that is known to possess such homogeneous recessive gene pair and observing the phenotype for elevated palmitic acid content in subsequent generations while confirming the mode of inheritance for such trait. When the fap5fap5 gene pair is present in a given plant and is crossed with A27 or other confirmed source for the requisite gene pair, all offspring will express the elevated palmitic acid content in the next generation in the absence of segregation.

It further has been found that the presence of the homogeneous recessive fap5fap5 gene pair in an otherwise conventional soybean plant in addition to raising the palmitic acid content of the endogenously formed vegetable oil of the seeds has tended to leave the concentration of the stearic acid (C18:0) component of the vegetable oil substantially unchanged, to raise the oleic acid (Cl8:1) concentration approximately 2 to 5 percent by weight, to lower the linoleic acid (C18:2) concentration approximately 2 to 8 percent by weight, and to lower the linolenic acid (C18:3) concentration approximately 1 percent by weight. Such modification of the fatty acid profile in the resulting vegetable oil derived from soybean seeds made possible through the expression of the fap5fap5 gene pair accordingly is considered to be complex and to be incapable of simple explanation particularly in view of the manner in which concentrations of other fatty acids of the vegetable oil also are modified.

When the fap5fap5 gene pair is combined in a single soybean plant with the previously reported homogeneous recessive gene pairs (1) fap2fap2 or fap2-bfap2-b, and (2) fap4fap4 for the expression of elevated palmitic acid content, the expression of such gene pairs is additive in nature and results in the expression of a palmitic acid content that commonly exceeds that which previously has been reported in soybean seeds. The resulting palmitic acid concentration of the vegetable oil accordingly is greater than that of any of the source plants that initially provided the three recessive gene pairs or a combination of two of such gene pairs. In a preferred embodiment gene pair (1) is fap2-bfap2-b.

When the homogeneous recessive gene pairs (1) fap2-bfap2-b, (2) fap4fap4, and (3) fap5fap5 are combined in a soybean plant, the palmitic acid concentration in the resulting vegetable oil commonly is in excess of 30 up to approximately 37 percent by weight based on the total fatty acid content. Such vegetable oil additionally commonly contains based upon the total fatty acid content approximately 2.5 to 4.5 percent by weight stearic acid (C18:0), approximately 8 to 13 percent oleic acid (C18: 1), approximately 38 to 43 percent by weight linoleic acid (C18:2), and approximately 10 to 15 percent by weight linolenic acid (C18:3).

The fap2fap2 gene pair was developed at Purdue University through the treatment of the 'Century' cultivar with ethyl methanesulfonate (EMS) and as previously indicated is discussed in "Inheritance of Altered Palmitic Acid Percentage in Two Soybean Mutants", by E. A. Erickson appearing in the *Journal of Heredity*, Vol. 79, Pages 465 to 468 (1988). Seeds containing this fap2fap2 genetic determinant have been distributed widely by the U.S.D.A. and have been available to the public since 1990 from Curator, Soybean Germplasm Collection, USDA-ARS, Department of Agronomy, 1102 S. Goodwin, University of Illinois, Urbana, Ill. 61801, U.S.A. under the C1727 designation. Such C1727 bears Reg. No. GP-117 and PI532834 as reported in *Crop Science*, Vol. 30, Page 240 (January–Febuary, 1990).

The more preferred fap2-bfap2-b gene pair for use in the present technology was developed at Iowa State University through the treatment of the 'A1937' cultivar with N-nitroso-N-methylurea (NMU) and as previously indicated is discussed in "Inheritance of Elevated Palmitic Acid Content in Soybean Seed Oil", by W. R. Fehr et al. appearing in *Crop Sci.*, Vol. 31, Pages 1522 to 1524 (1991).

The fap4fap4 gene pair likewise was developed at Iowa State University through the treatment of the 'Elgin' cultivar with ethyl methanesulfonate (EMS) and as previously indicated is discussed in the same article appearing in *Crop Sci.*, Vol. 31, Pages 1522 to 1524 (1991).

A soybean plant initially designated A1937NMU-85 and subsequently designated A21 containing the fap2-bfap2-b gene pair was crossed with a soybean plant designated ElginEMS-421 containing the fap4fap4 gene pair, and following self-pollination and selection in subsequent generations a plant was produced containing the fap2-bfap2-b and fap4fap4 gene pairs as described in the above-identified article appearing in *Crop. Sci.*, Vol. 31, Pages 1522 to 1524 (1991). The resulting plant initially was designated AX4663-5-4-5 and subsequently was redesignated as A19 as previously indicated. 2,500 seeds of A1937 NMU-85 containing the fap2-bfap2-b gene pair were deposited on Jan. 18, 1996 under the terms of the Budapest Treaty at the American Type Culture Collection (ATCC) at 12301 Parklawn Drive, Rockville, Md. 20852, U.S.A., and have been assigned ATCC Accession No. 97618. 2,500 seeds of Elgin NMU-421 containing the fap4fap4 gene pair were deposited on Jan. 18, 1996 under the terms of the Budapest Treaty at the same depository and have been assigned ATCC Accession No. 97617. 2,500 seeds of AX4663-5-4-5 containing the fap2-bfap2-b gene pair and the fap4fap4 gene pair were deposited on Dec. 26, 1995 under the terms of the Budapest Treaty at the same depository, and have been assigned ATCC Accession No. 97393. Such AX4663-5-4-5 line also is identified in commonly assigned Ser. Nos. 08/375,340 filed Jan. 19, 1995 (now U.S. Pat. No. 5,557, 039), and 08/376,466 filed Jan. 20, 1995 (now U.S. Pat. No. 5,602,311), which are herein incorporated by reference. Seeds from these deposits will be irrevocably made available upon the maturation of a patent application that makes reference to same into a patent. However, the availability of these seeds is not to be construed as a license to practice a claimed invention in contravention of rights granted under the authority of any government in accordance with its patent or breeder's rights laws.

The fap5fap5 genetic determinant for elevated palmitic acid content in the endogenously produced vegetable oil derived from soybeans is heritable and can be readily and reliably transferred to other soybean lines and cultivars alone or in combination with the other recessive gene pairs discussed herein by conventional plant breeding. Following the initial cross with or without further backcrossing, desired segregants are selected and are preserved following self-pollination in subsequent generations that possess the requisite phenotype for elevated palmitic acid production and the requisite homogeneous recessive gene pair (ie., fap5fap5) or gene pairs (ie., fap2-bfap2-b, fap4fap4, and fap5fap5). Such genetic determinants are heritable independent of each other. Accordingly, the requisite gene pair or gene pairs can be provided in descendants of the original plants formed through simple self-pollination or through cross-pollination with other soybean lines and cultivars followed by a further selection of the desired segregants.

The endogenously formed vegetable oil of the present invention can be derived or removed from the resulting soybean seeds by conventional means, such as by simple crushing and preferably by crushing as well as extraction (e.g., with hexane).

The soybean vegetable oil of the present invention in view of the elevated palmitic acid content is particularly suited for use in industrial and food applications where the additional palmitic acid concentration is advantageous because of its influence on the properties of the product to be formed. When the oil was endogenously formed while under the influence of the combined presence of the three homogeneous recessive gene pairs, the level of palmitic acid can be sufficiently raised to facilitate the formation of margarine therefrom in the absence of hydrogenation. The ability to avoid hydrogenation provides readily apparent economic advantages and obviates the formation of trans-fatty acids which some consumers prefer to minimize in the diet. The oil also is well suited for the formation of shortening. Such elevated saturated fatty acid content also confers stability against oxidation, and enhances usefulness in frying applications.

All fatty acid concentrations discussed herein were determined through the use of gas liquid chromatography as described by E. G. Hammond in "Organization of Rapid Analysis of Lipids in Many Individual Plants", Pages 321 to 330 (1991) appearing in H. F. Liskins and J. F. Jackson (ed.) "Essential Oils and Waxes. Modern Methods of Plant Analysis", Vol. 12, Springer-Verlag, Berlin. Prior to the analysis, the vegetable oil was obtained by crushing the seed in a hydraulic press at $3.4 \times 10^6$ Pa, and was further extracted with distilled hexane. During such determination the glycerol esters present in the vegetable oil were converted to methyl esters by the use of sodium methoxide in methanol, and the methyl esters separated and quantified by gas liquid chromatography to provide the fatty acid concentrations specified.

The following Examples are presented as specific illustrations of the claimed invention. It should be understood however that the invention is not limited to the specific details set forth in the Examples.

EXAMPLE I

Seeds of the 'Kenwood' cultivar of Glycine max L. Merr. were selected as the starting material. This soybean cultivar is known for its good agronomic qualities when grown in the central region of United States and was registered during 1990 by the Crop Science Society of America. This starting material bears Reg. No. 253 and PI537094 and is discussed in Crop Science, Vol. 30, Page 1162 (September–October 1990). Seeds of this cultivar are available to the public from the Committee for Agricultural Development, Ames, Iowa 50011, U.S.A.

A representative sample of 2,500 mature seeds of the 'Kenwood' cultivar was soaked in 2.5 liters of distilled water at room temperature for 8 hours with aeration, and the water was drained from the seeds. The seeds were next soaked for 9 hours at room temperature in 2.5 liters of an aqueous 0.1M. phosphate buffer containing a 0.025 M. solution of ethyl methanesulfonate (EMS). The solution was drained from the seeds and the seeds were rinsed twice with distilled water. The wet seeds were next immediately planted in the field at Ames, Iowa. The plants resulting from the germination of such seeds were considered to be the M1 generation and were designated Kenwood EMS. Seeds were formed on such M1 plants following self-pollination and were designed the M2 generation. An equal number of M2 seeds was harvested from each M1 plant and the seeds were bulked to obtain 2,000 seeds which next were planted in Puerto Rico. One pod containing M3 seeds was harvested following self-pollination from each M2 plant and the M3 seeds were bulked. Next 1,000 of the M3 seeds from the Kenwood EMS population, as well as seeds of the 'Kenwood' cultivar, were planted. Seeds formed on 500 randomly selected M3 plants and on 4 'Kenwood' plants and were individually harvested.

A representative sample of the matre seeds of the 'Kenwood' cultivar that had not undergone mutagenesis was found to exhibit the fatty acid profile reported in the following Table A:

TABLE A

| Fatty Acid | Number of Carbon Atoms Per Molecule | Number of Double Bonds Per Molecule | Weight Percent |
|---|---|---|---|
| Palmitic | 16 | 0 | 12.1 |
| Stearic | 18 | 0 | 4.5 |
| Oleic | 18 | 1 | 21.7 |
| Linoleic | 18 | 2 | 55.0 |
| Linolenic | 18 | 3 | 6.8 |

When M4 seeds from Kenwood EMS M3 plants were analyzed for fatty acid concentration, a plant designed Kenwood EMS-528 was found to exhibit a mean elevated palmitic acid content as reported in the following Table B:

TABLE B

| Fatty Acid | Number of Carbon Atoms Per Molecule | Number of Double Bonds Per Molecule | Weight Percent |
|---|---|---|---|
| Palmitic | 16 | 0 | 15.8 |
| Stearic | 18 | 0 | 3.8 |
| Oleic | 18 | 1 | 19.6 |
| Linoleic | 18 | 2 | 53.6 |
| Linolenic | 18 | 3 | 7.4 |

Such Kenwood EMS-528 M4 seeds were found to possess the homogeneous recessive fap5fap5 gene pair for elevated palmitic acid production, and was redesignated as A27.

Following the formation of another generation via self-pollination under the same field growing conditions in Puerto Rico, mature M5 seeds of A27 possessing the fap5fap5 gene pair and of the original 'Kenwood' cultivar were analyzed for fatty acid composition. The mean results for 'Kenwood' cultivar that had not undergone mutagenesis are reported in Table C, and for A27 are reported in Table D.

TABLE C

| Fatty Acid | Number of Carbon Atoms Per Molecule | Number of Double Bonds Per Molecule | Weight Percent |
|---|---|---|---|
| Palmitic | 16 | 0 | 12.7 |
| Stearic | 18 | 0 | 4.3 |
| Oleic | 18 | 1 | 21.7 |
| Linoleic | 18 | 2 | 53.9 |
| Linolenic | 18 | 3 | 7.4 |

TABLE D

| Fatty Acid | Number of Carbon Atoms Per Molecule | Number of Double Bonds Per Molecule | Weight Percent |
| --- | --- | --- | --- |
| Palmitic | 16 | 0 | 16.7 |
| Stearic | 18 | 0 | 3.9 |
| Oleic | 18 | 1 | 27.1 |
| Linoleic | 18 | 2 | 45.7 |
| Linolenic | 18 | 3 | 6.6 |

Such data demonstrates that the different elevated palmitic acid concentration in A27 attributable to the presence of the fap5fap5 gene pair is reliably transmitted to subsequent generations following self-pollination. 2,500 seeds of A27 were deposited on Aug. 28, 1997 under the terms of the Budapest Treaty at the American Type Culture Collection (ATCC) at 12301 Parklawn Drive, Rockville, Md. 20852, U.S.A. and have been assigned ATCC Accession No. 209,222.

EXAMPLE II

A27 bearing the fap5fap5 gene pair next was crossed at Ames, Iowa, with a plant of A19 (previously discussed) that possessed the homogeneous recessive gene pairs fap2-bfap2-b and fap4fap4, but lacked the fap5fap5 gene pair. Plants of A19 that were utilized in such cross possessed the fatty acid profile reported in the following Table E.

TABLE E

| Fatty Acid | Number of Carbon Atoms Per Molecule | Number of Double Bonds Per Molecule | Weight Percent |
| --- | --- | --- | --- |
| Palmitic | 16 | 0 | 27.9 |
| Stearic | 18 | 0 | 3.9 |
| Oleic | 18 | 1 | 13.2 |
| Linoleic | 18 | 2 | 44.9 |
| Linolenic | 18 | 3 | 10.2 |

The resulting $F_1$ plants subsequently were self-pollinated and $F_2$ segregants were selected and preserved that possessed in combination homogeneous recessive gene pairs of (1) fap2-bfap2-b, (2) fap4fap4, and (3) fap5fap5. One of these selections designated A28 was found to exhibit the following fatty acid profile as reported in Table F.

TABLE F

| Fatty Acid | Number of Carbon Atoms Per Molecule | Number of Double Bonds Per Molecule | Weight Percent |
| --- | --- | --- | --- |
| Palmitic | 16 | 0 | 34.7 |
| Stearic | 18 | 0 | 3.0 |
| Oleic | 18 | 1 | 10.4 |
| Linoleic | 18 | 2 | 40.0 |
| Linolenic | 18 | 3 | 12.0 |

It will be noted that the palmitic acid (C16:0) concentration of A28 exceeded that of A19 by approximately 7 percent by weight based upon the total fatty acid content. 2,500 seeds of A28 were deposited on Aug. 5, 1996 under the terms of the Budapest Treaty at the American Type Culture Collection (ATCC) at 12301 Parklawn Drive, Rockville, Md. 20852, U.S.A. and have been assigned ATCC Accession No. 97,672. Seeds from such deposit will be irrevocably made available upon the grant of a patent that makes reference to such deposit. However, the availability of these seeds is not to be construed as a license to practice the claimed invention in contravention of rights granted under the authority of any government in accordance with its patent or breeder's rights laws.

Although the invention has been described with reference to preferred embodiments, it is to be understood that variations and modifications may be resorted to as will be apparent to those skilled in the art. Such variations and modifications are to be considered within the purview and scope of the claims appended hereto.

We claim:

1. A vegetable oil possessing an elevated palmitic acid content following removal from a soybean seed wherein said palmitic acid concentration is attributable to the combined presence of the homogeneous recessive gene pairs (1) fap2fap2 or fap2-bfap2-b, (2) fap4fap4, and (3) fap5fap5.

2. A vegetable oil possessing an elevated palmitic acid content according to claim 1 following removal from a soybean seed wherein said palmitic acid concentration is enhanced by the combined presence of the homogeneous recessive gene pairs (1) fap2-bfap2-b, (2) fap4fap4, and (3) fap5fap5.

3. A vegetable oil possessing an elevated palmitic acid content following removal from a soybean seed wherein said palmitic acid concentration is attributable to the combined presence of the homogeneous recessive gene pairs (1) fap2-bfap2-b, (2) fap4fap4, and (3) fap5fap5 that are present in A28 having ATCC Accession No. 97,672.

4. A vegetable oil possessing an elevated palmitic acid content following removal from a soybean seed of A28 having ATCC Accession No. 97,672 possessing in combination the homogeneous recessive gene pairs (1) fap2-bfap2-b, (2) fap4fap4, and fap5fap for the expression of said elevated palmitic acid content, or soybean seeds descended therefrom that possess said homogeneous recessive gene pairs.

5. A vegetable oil according to claim 1 wherein said elevated palmitic acid content of said vegetable oil of said seeds is in excess of 30 up to approximately 37 percent by weight based on the total fatty acid content as determined by gas liquid chromatography.

6. A vegetable oil according to claim 2 wherein said elevated palmitic acid content of said vegetable oil of said seeds is in excess of 30 up to approximately 37 percent by weight based on the total fatty acid content as determined by gas liquid chromatography.

* * * * *